(12) United States Patent
Manku et al.

(10) Patent No.: US 9,096,815 B2
(45) Date of Patent: Aug. 4, 2015

(54) COMPOSITIONS COMPRISING 20-CARBON FATTY ACIDS AND METHODS OF MAKING AND USING SAME

(71) Applicant: Dignity Sciences Limited, Dublin (IE)

(72) Inventors: Mehar Manku, England (GB); Jonathan Rowe, Waterford, CT (US); John Climax, Dublin (IE)

(73) Assignee: Dignity Sciences Limited, Dublin (IE)

( * ) Notice: Subject to any disclaimer, the term of this patent is extended or adjusted under 35 U.S.C. 154(b) by 170 days.

(21) Appl. No.: 13/688,998

(22) Filed: Nov. 29, 2012

(65) Prior Publication Data

US 2013/0331448 A1   Dec. 12, 2013

Related U.S. Application Data

(60) Provisional application No. 61/711,585, filed on Oct. 9, 2012, provisional application No. 61/564,652, filed on Nov. 29, 2011.

(51) Int. Cl.
| | | |
|---|---|---|
| C11B 1/00 | (2006.01) | |
| A61K 31/20 | (2006.01) | |
| C12P 7/64 | (2006.01) | |
| C11C 3/00 | (2006.01) | |

(52) U.S. Cl.
CPC ................. *C11C 3/00* (2013.01); *C12P 7/6409* (2013.01); *C12P 7/6427* (2013.01); *C12P 7/6436* (2013.01)

(58) Field of Classification Search
CPC ....... A61K 31/20; A61K 31/19; A61Q 19/00; A63L 1/3008; A23K 1/164; C11B 1/04; C11B 1/10; C11B 1/00; C11B 1/08; B01D 11/0203

USPC ........ 435/134; 514/558; 554/11, 12, 161, 170
See application file for complete search history.

(56) References Cited

U.S. PATENT DOCUMENTS

| | | | |
|---|---|---|---|
| 2008/0125487 A1 | 5/2008 | Das et al. | |
| 2008/0213357 A1* | 9/2008 | Hebard et al. | 424/456 |
| 2009/0176284 A1* | 7/2009 | Furihata et al. | 435/134 |
| 2011/0015415 A1 | 1/2011 | Singh et al. | |
| 2011/0016585 A1* | 1/2011 | Pereira et al. | 800/281 |
| 2011/0039010 A1 | 2/2011 | Rein et al. | |
| 2013/0331448 A1 | 12/2013 | Manku et al. | |

FOREIGN PATENT DOCUMENTS

WO   WO 2013/082265   6/2013

OTHER PUBLICATIONS

Xue et al., "Optimization of Synthetic Conditions for the Preparation of Dihomo- 9. gamma-Linolenic Acid from gamma-Linolenic Acid," Journ Amer. Oil Chemists' Soc, Jan. 2009, vol. 86, Issue 1, pp. 77-82.*

Xue et al., "Optimization of Synthetic Conditions for the Preparation of Dihomo-gamma-Linolenic Acid from gamma-Linolenic Acid," Journ Amer. Oil Chemists' Soc., Jan. 2009, vol. 86, Issue 1, pp. 77-82.

PCT/US2012/67030 International Search Report dated Feb. 5, 2013.

* cited by examiner

*Primary Examiner* — Deborah D Carr

(74) *Attorney, Agent, or Firm* — Perkins Coie LLP

(57) ABSTRACT

The present disclosure provides a process for producing 20-carbon fatty acids from a plant seed oil, the process comprising: a) providing a plant seed oil comprising fatty acids, wherein the fatty acids include 18-carbon fatty acids; and b) elongating the fatty acids by two carbon atoms to produce a composition comprising 20-carbon fatty acids.

24 Claims, 1 Drawing Sheet

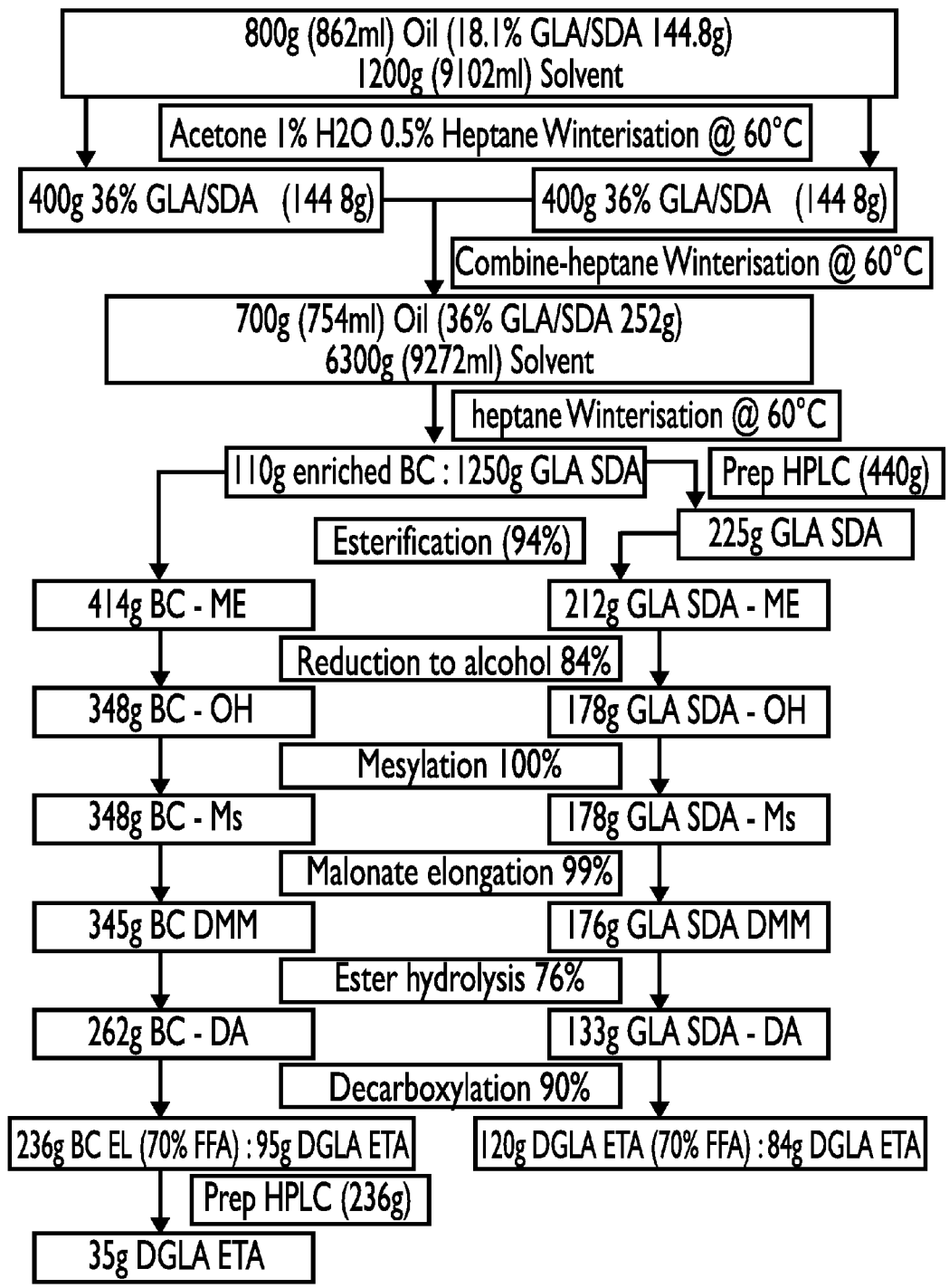

COMPOSITIONS COMPRISING 20-CARBON FATTY ACIDS AND METHODS OF MAKING AND USING SAME

PRIORITY CLAIM

This application claims priority from U.S. provisional patent application 61/711,585, filed Oct. 9, 2012, and U.S. provisional patent application 61/564,652, filed Nov. 29, 2011, each of which are incorporated herein by reference in their entireties.

FIELD

The invention generally relates to compositions comprising 20-carbon fatty acids and methods of manufacture and use.

SUMMARY

The present disclosure provides processes for producing compositions comprising 20-carbon fatty acids from an oil (such as a plant seed oil) comprising 18-carbon fatty acids. The process generally involves elongating two or more different 18-carbon fatty acids by two carbon atoms, wherein 20-carbon fatty acids are produced from the 18-carbon fatty acids. In some embodiments, more than one 18-carbon fatty acid is elongated by two carbon atoms in a single reaction (e.g., a single-pot reaction). In some embodiments, the 18-carbon fatty acids comprise stearidonic acid ("SDA"), alpha linolenic acid ("ALA") and gamoleic acid (also referred to as gamma-linolenic acid or GLA). In some embodiments, the 20-carbon fatty acids comprise eicosatetraenoic acid ("ETA"), eicosatrienoic acid ("ETE") and dihomo-gamma-lineoleic acid ("DGLA").

In various embodiments, the process comprises the steps of (a) providing an oil comprising 18-carbon fatty acids and/or 18-carbon fatty acid triglycerides (e.g., a plant seed oil such as black currant oil), (b) saponifying the 18-carbon fatty acid esters and/or the 18-carbon fatty acid triglycerides to form a composition comprising 18-carbon free fatty acids, (c) optionally concentrating one or more of the 18-carbon fatty acids, (d) elongating the 18-carbon free fatty acids to produce a composition comprising 20-carbon fatty acids, and (e) optionally concentrating one or more of the 20-carbon fatty acids to produce an enriched composition comprising 20-carbon fatty acids.

In some embodiments, the composition comprising 18-carbon free fatty acids is concentrated in step (c) by a method comprising at least one crystallization step. In some embodiments, step (c) comprises: (i) a first crystallization step using a first solvent system, and (ii) a second crystallization step using a second solvent system. In some embodiments, the first and second solvent systems are the same. In some embodiments, the first and second solvent systems are different. In some embodiments, the first solvent system comprises acetone, water and a non-polar aprotic solvent such as heptane. In some embodiments, the second solvent system comprises a non-polar aprotic solvent such as heptane. In some embodiments, the composition after step (c) contains more 18-carbon fatty acid compounds compared to the composition before step (c). In some embodiments, the amount of 18-carbon fatty acids in the composition after step (c) is about 1.1 times to about 10 times the amount of 18-carbon fatty acids in the composition before step (c). In some embodiments, the composition comprises 18-carbon fatty acids in an amount of about 18% to about 80%, for example about 50% or more. In some embodiments, the amount of linoleic acid in the composition is reduced by about 25% or more, for example by about 50%.

In some embodiments, the fatty acids in the oil comprises a mixture of omega-3 and omega-6 fatty acids.

In some embodiments, two or more 18-carbon fatty acids and/or 18-carbon fatty acid triglycerides in the oil are elongated simultaneously.

In some embodiments, elongation of the 18-carbon free fatty acids in step (d) occurs by: (i) esterification of the 18-carbon free fatty acids to form 18-carbon fatty acid esters; (ii) reduction of the 18-carbon fatty acid esters to form 18-carbon fatty acid primary alcohols; (iii) conversion of the primary alcohol motif on the 18-carbon fatty acid primary alcohols into a primary leaving group (e.g., a mesylate) to form 18-carbon fatty acid electrophiles; (iv) reaction of the resulting 18-carbon fatty acid electrophiles with a nucleophile such as deprotonated dimethyl malonate (DMM:$^-$); and (v) if the nucleophile is DMM:$^-$ or a similar deprotonated diester, hydrolysis of the diester to form the corresponding di-acid, followed by decarboxylation to form a composition comprising 20-carbon free fatty acids. In some embodiments, the composition comprises at least about 35% 20-carbon free acids, for example about 50%.

In some embodiments, the 18-carbon fatty acids and/or 18-carbon fatty acid triglycerides comprise one or more of SDA, GLA, and ALA.

In some embodiments, the 20-carbon fatty acids comprise one or more of ETA, ETE and DGLA.

In some embodiments, the process further comprises extracting at least a portion of the 18-carbon fatty acids from the oil prior to elongation of the fatty acids by two carbon atoms. In some embodiments, the step of extracting comprises an organic solvent extraction or a $CO_2$ supercritical fluid extraction ($CO_2$-SFE).

In some embodiments, the process further comprises purifying or concentrating the 20-carbon fatty acids. In some embodiments, the step of purifying the 20-carbon fatty acids comprises urea fractionation, low-temperature crystallization, chromatographic separation such as HPLC, or distillation.

In some embodiments, at least a portion of the 18-carbon fatty acids are elongated by two carbon atoms by contacting the 18-carbon fatty acids with an enzyme such as elongase.

In some embodiments, at least a portion of the 18-carbon fatty acids are chemically elongated by two carbon atoms by, for example, contacting the 18-carbon fatty acids with a reducing agent, brominating the resulting primary alcohols, coupling the bromides with a $C_2$-elongation block such as an optionally substituted oxazoline, and converting the elongated oxazoline to form 20-carbon fatty acids.

In some embodiments, the 20-carbon fatty acids are concentrated or purified to produce 20-carbon fatty acids having a purity of at least 30%, at least 40%, at least 50%, at least 60%, at least 70%, at least 80%, at least 90%, or greater than 90%.

In some embodiments the purified 20-carbon fatty acids are then contacted with or exposed to the enzyme 15-lipoxygenase. In some embodiments the fatty acids produced from contact with or exposure to 15-lipoxygenase are 15-HETrE and/or 15-OH-ETA. In one embodiment, the ratio of 15-HETrE to 15-OH-ETA produced by contact with or exposure to 15-lipoxygenase is about 10:1 to about 1:10 or 5:1 to about 1:5.

In some embodiments, the oil comprising 18-carbon fatty acids and/or 18-carbon fatty acid triglycerides is a plant seed oil is selected from the group comprising: Echium seed oil, blackcurrant seed oil, borage seed oil, evening primrose seed oil, hackelia seed oil, trichodesma seed oil, buglossoides seed oil, and combinations thereof.

In some embodiments, the process further comprises deodorizing the 20-carbon fatty acids. In some embodiments, deodorizing comprises mixing the 20-carbon fatty acids with a mixture of silica and charcoal or passing the 20-carbon fatty acids through a celite filter.

In some embodiments, the process further comprises esterifying (e.g. contacting 18- or 20-carbon fatty acid(s) with an alcohol and an acid) to produce fatty acid esters. In one embodiment, esterified 20-carbon fatty acids are concentrated from said esterified fatty acids. In other embodiments, DGLA esters, ETE esters, ETA esters, 15-HETrE esters and/or 15-OH-ETA esters are concentrated from said esterified fatty acids.

In some embodiments, the esterified fatty acids (e.g. DGLA, ETE, ETA, 15-HETrE and 15-OH-ETA esters) are selected from the group consisting of alkyl esters, heteroalkyl esters, aryl esters, heteroaryl esters, methyl esters, ethyl esters, propyl esters, isopropyl esters, butyl esters, isobutyl esters, t-butyl esters, and combinations thereof.

In some embodiments, the ratio of produced 20-carbon fatty acids to starting 18-carbon fatty acids remains substantially the same as said ratio in the starting oil. In other embodiments, the ratio of produced 20-carbon fatty acids to starting 18-carbon fatty acids is about 1:10 to about 10:1, about 1:5 to about 5:1, about 1:2 to about 2:1 or about 1:1. In one embodiment, the ratio of DGLA:ETA remains substantially the same as the ratio of GLA:SDA in the starting oil. In another embodiment the ratio of DGLA:ETE:ETA remains substantially the same as the ratio of GLA:ALA:SDA in the starting oil. In another embodiment the ratio of DGLA to the sum of ETE and ETA remains substantially the same as the ratio of GLA to the sum of ALA and SDA in the starting oil. In another embodiment the ratio of DGLA to the sum of ETE and ETA increases as compared to the ratio of GLA to the sum of ALA and SDA in the starting oil. In another embodiment, the ratio of 15-HETrE 15-OH-ETA remains substantially the same as the ratio of GLA:SDA in the starting oil.

The present disclosure also provides a composition comprising fatty acids produced by any of the processes disclosed herein. In some embodiments, the composition comprises at least 30%, at least 40%, at least 50%, at least 60%, at least 70%, at least 80%, at least 90%, or greater than 90% DGLA. In some embodiments, the composition comprises at least 30%, at least 40%, at least 50%, at least 60%, at least 70%, at least 80%, at least 90%, or greater than 90% ETA. In some embodiments, the composition comprises at least 30%, at least 40%, at least 50%, at least 60%, at least 70%, at least 80%, at least 90%, or greater than 90% ETE. In some embodiments, the composition comprises at least 30%, at least 40%, at least 50%, at least 60%, at least 70%, at least 80%, at least 90%, or greater than 90% 15-HETrE. In some embodiments, the composition comprises at least 30%, at least 40%, at least 50%, at least 60%, at least 70%, at least 80%, at least 90%, or greater than 90% 15-OH-ETA.

In one embodiment, the present disclosure provides processes for producing a composition comprising DGLA and ETA by providing a plant seed oil comprising fatty acids, wherein the fatty acids include SDA and GLA; extracting SDA and GLA from the plant seed oil; elongating the SDA and GLA (in the same reaction vessel at the same time, substantially simultaneously or simultaneously) by two carbon atoms, wherein DGLA and ETA are produced from SDA and GLA; and purifying and/or concentrating the DGLA and/or ETA.

In another embodiment, the present disclosure provides processes for producing a composition comprising DGLA, ETE and ETA by providing a plant seed oil comprising fatty acids, wherein the fatty acids include ALA, SDA and GLA; extracting ALA, SDA and GLA from the plant seed oil; elongating the ALA, SDA and GLA (in the same reaction vessel at the same time, substantially simultaneously or simultaneously) by two carbon atoms to produce ETE, ETA and DGLA, respectively; and purifying and/or concentrating the DGLA, ETA and/or ETA.

In another embodiment, the present disclosure provides processes for producing a composition comprising 15-HETrE and 15-OH-ETA by providing a plant seed oil comprising fatty acids, wherein the fatty acids include SDA and GLA; extracting SDA and GLA from the plant seed oil; elongating the SDA and GLA (in the same reaction vessel at the same time, substantially simultaneously or simultaneously) by two carbon atoms, wherein DGLA and ETA are produced from SDA and GLA; contacting or exposing the DGLA and ETA with 15-lipoxygenase to form 15-HETrE and/or 15-OH-ETA, and purifying/concentrating the 15-HETrE and/or 15-OH-ETA.

The present disclosure also provides compounds, compositions and pharmaceutical compositions produced by the aforementioned processes. In some embodiments, the composition comprises at least 50 wt. % of DGLA, ETE, ETA, or a combination thereof. In some embodiments, the composition comprises a ratio of DGLA to ETA of about 1:8 to about 8:1, for example about 1:1. In some embodiments, the composition comprises a ratio of DGLA to the sum of ETE and ETA of about 1:8 to about 8:1, for example about 1:1. In some embodiments, the composition comprises at least 50 wt. % of 15-HETrE, 15-OH-ETA or a combination thereof. In some embodiments, the composition comprises a ratio of 15-HETrE to 15-OH-ETA of about 1:8 to about 8:1, for example about 1:1.

BRIEF DESCRIPTION OF THE FIGURES

FIG. 1 depicts a flow diagram for one embodiment of a process for producing 20-carbon fatty acids from an oil comprising 18-carbon fatty acids and/or 18-carbon fatty acid triglycerides.

DETAILED DESCRIPTION

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Dihomo-gamma-linolenic acid, also known as cis-8,11,14-eicosatrienoic acid or C 20:3ω6 ("DGLA"), is the elongation product of gamma-linolenic acid, also referred to as gamoleic acid or C 18:3ω6 ("GLA"). GLA is a component of natural oils from a variety of plants such as Echium, blackcurrant, borage, evening primrose, hackelia, trichodesma, and buglossoides, to name a few. As used herein, the term "GLA" refers to GLA triglyceride, free acid (e.g., cis-6,9,12-octadecatrienoic acid) and/or a pharmaceutically acceptable ester, derivative, conjugate or salt thereof, or mixtures of any of the foregoing. In some embodiments, GLA is in the form of a $C_{1-4}$ alkyl ester such as methyl ester or ethyl ester form. As used herein, the term "DGLA" refers to DGLA free acid (e.g., cis-8,11,14-eicosatrienoic acid) and/or a pharmaceutically acceptable ester, derivative, conjugate or salt thereof, or mixtures of any of the foregoing. In some embodiments, DGLA is in the form of a $C_{1-4}$ alkyl ester such as methyl ester or ethyl ester form.

Stearidonic acid is also known as all-cis-6,9,12,15-octadecatetraenoic acid or C 18:4ω3 ("SDA"). As used herein, the term "SDA" refers to SDA triglycerides, free acid and/or a pharmaceutically acceptable ester, derivative, conjugate or salt thereof, or mixtures of any of the foregoing. In some embodiments, SDA is in the foam of a $C_{1-4}$ alkyl ester such as methyl ester or ethyl ester form.

15-Hydroxy-eicosa-8(Z),11(Z),13(E)-trienoic acid ("15-HETrE") is a derivative of DGLA. As used herein, the term "15-HETrE" refers to 15-HETrE in its free acid form (e.g., 15-hydroxy-eicosa-8(Z),11(Z),13(E)-trienoic acid) and/or a pharmaceutically acceptable ester, derivative, conjugate or salt thereof, or mixtures of any of the foregoing.

Eicosatetraenoic acid ("ETA"), also known as all-cis-8,11,14,17-eicosatetraenoic acid or 20:4ω3, is the elongation product of stearidonic acid. As used herein, the term "ETA" refers to ETA free acid and/or a pharmaceutically acceptable ester, derivative, conjugate or salt thereof, or mixtures of any of the foregoing. In some embodiments, ETA is in the form of a $C_{1-4}$ alkyl ester such as methyl ester or ethyl ester form.

15-Hydroxy eicosatetraenoic acid (15-Hydroxy-5,8,11,13-eicosatetraenoic acid; referred to herein as "15-OH-ETA") is a derivative of ETA. As used herein, the term "15-OH-ETA" refers to 15-OH-ETA free acid and/or a pharmaceutically acceptable ester, derivative, conjugate or salt thereof, or mixtures of any of the foregoing. In some embodiments, 15-OH-ETA is in the form of a $C_{1-4}$ alkyl ester such as methyl ester or ethyl ester form.

α-linolenic acid is also known as all-cis-9,12,15-octadecatrienoic acid or 18:3ω3 ("ALA"). As used herein, the term "ALA" refers to ALA triglycerides, free acid and/or a pharmaceutically acceptable ester, derivative, conjugate or salt thereof, or mixtures of any of the foregoing. In some embodiments, ALA is in the form of a $C_{1-4}$ alkyl ester such as methyl ester or ethyl ester form.

Eicosatrienoic acid ("ETE"), also known as all-cis-11,14,17-eicosatrienoic acid or 20:3ω3, is the elongation product of ALA. As used herein, the term "ETE" refers to ETE free acid and/or a pharmaceutically acceptable ester, derivative, conjugate or salt thereof, or mixtures of any of the foregoing. In some embodiments, ETE is in the form of a $C_{1-4}$ alkyl ester such as methyl ester or ethyl ester form.

As used herein, the terms "DGLA derivative" and "derivative of DGLA" refer to compounds formed from the chemical conversion of DGLA including, without limitation, 15-HETrE, and esters, derivatives, conjugates or salts thereof, or mixtures of any of the foregoing. One of skill in the art will readily recognize from the chemical structure and other properties whether a given compound is a DGLA derivative.

The fatty acid content of any composition disclosed herein can be determined by any suitable method known in the art. For example and without limitation, the fatty acid content of a composition disclosed herein may be determined by gas chromatography. In one embodiment, a method for determining the fatty acid content of a composition comprises injection of a sample (e.g., a 1 μL bolus) of the composition into a gas chromatography system equipped with a DB-FFAP 30 m×250 μm column having a 0.5 mm film thickness placed inside a chamber/oven, an FID detector set at 300° C., an inert carrier gas (e.g., helium) with a flow rate of about 1.0 mL/min. The temperature of the column may be maintained at a suitable temperature, or may be increased over time (e.g., "ramped") from an initial temperature of, for example, about 180° C. to a final, higher temperature of, for example, about 250° C. over the course of several minutes (e.g., a ramp of 70° C. over 7 minutes, or about 10° C./minute). One skilled in the art will recognize, however, that other GC columns and conditions are readily substitutable for the exemplary conditions disclosed herein.

In one embodiment, DGLA, ETE, ETA, 15-OH-ETA, and/or 15-HETrE are deodorized prior to use in a method or composition as disclosed herein. In one embodiment, an oil containing (1) DGLA and ETA or an oil containing (2) 15-HETrE and 15-OH-ETA or an oil containing (3) DGLA, ETE and ETA is mixed with silica and charcoal. In one embodiment, the silica and charcoal are in a ratio of about 1:1 to about 50:1, for example about 1:1, about 2:1, about 3:1, about 4:1, about 5:1, about 6:1, about 7:1, about 8:1, about 9:1, about 10:1, about 12:1, about 14:1, about 15:1, about 16:1, about 18:1, about 20:1, about 25:1, about 30:1, about 35:1, about 40:1, about 45:1, or about 50:1. In one embodiment, the ratio of DGLA (or 15-OH-ETA or 15-HETrE) to silica/charcoal is about 1:1 to about 50:1, for example about 1:1, about 2:1, about 3:1, about 4:1, about 5:1, about 6:1, about 7:1, about 8:1, about 9:1, about 10:1, about 12:1, about 14:1, about 15:1, about 16:1, about 18:1, about 20:1, about 25:1, about 30:1, about 35:1, about 40:1, about 45:1, or about 50:1. In one embodiment, crude DGLA, 15-OH-ETA, and/or 15-HETrE has been deodorized by filtering over a CELITE filter. In another embodiment, lecithin is used in the deodorizing of the fatty acids.

Elongation of 18-Carbon Fatty Acids

In some embodiments, at least a portion of the 18-carbon fatty acids are elongated by two carbon atoms by contacting the 18-carbon fatty acids with an enzyme such as elongase.

In some embodiments, at least a portion of the 18-carbon fatty acids are chemically elongated by two carbon atoms by, for example, contacting the 18-carbon fatty acids with a reducing agent to form primary alcohols, brominating the resulting primary alcohols, coupling the bromides with a $C_2$-elongation block such as an optionally substituted oxazoline, and converting the elongated oxazoline to form 20-carbon fatty acids.

In one such embodiment, 18-carbon fatty acids are first treated with lithium aluminum hydride to form the corresponding 18-carbon primary alcohols. The 18-carbon primary alcohols are then treated with triphenylphosphine dibromide ($Ph_3PBr_2$). The resulting bromides are then elongated by treatment with a mixture of 2,4,4-trimethyl-2-oxazoline and n-butyllithium to form dimethyloxazoline-protected 20-carbon fatty acids. Treatment with hydrochloric acid yields 20-carbon fatty acid methyl esters. The corresponding 20-carbon fatty acids can be formed by conventional hydrolysis methods, such as by treatment with KOH followed by acidic work-up.

In some embodiments, at least a portion of the 18-carbon fatty acids are chemically elongated by two carbon atoms by, for example, converting the 18-carbon fatty acids into their corresponding 18-carbon fatty acid esters, contacting the 18-carbon fatty acid esters with a reducing agent to form primary alcohols, mesylating the resulting primary alcohols to form mesylates, coupling the mesylates with a $C_2$-elongation block such as a di-alkyl malonate to form 20-carbon α-substituted fatty acid derivatives, hydrolyzing the 20-carbon α-substituted fatty acid derivatives to form 20-carbon α-carboxylated fatty acid derivatives, and decarboxylating the 20-carbon α-substituted fatty acid derivatives to form 20-carbon fatty acids.

In one such embodiment, the 18-carbon free fatty acids are esterified to form 18-carbon fatty acid esters such as methyl esters. The esters are treated with lithium aluminum hydride to form 18-carbon primary alcohols, which are then treated with methanesulfonyl chloride (mesyl chloride) to form 18-carbon primary mesylates. The 18-carbon primary mesylates are then treated with a solution containing deprotonated dimethyl malonate to form 20-carbon di-esters. The 20-carbon di-esters are hydrolyzed and then decarboxylated to form 20-carbon free fatty acids.

Enrichment of 18-Carbon Fatty Acids

In some embodiments, the oil comprising 18-carbon fatty acids (e.g., plant seed oil) is enriched such that the enriched oil contains comparatively more 18-carbon fatty acids than before the enrichment process is performed. The 18-carbon fatty acids in the enriched oil are then elongated to form 20-carbon fatty acids. In one such embodiment, the method for enriching the oil comprises separating at least a portion of fatty acids having more or less than 18 carbons (e.g., palmitic acid) from the oil. In one embodiment, the enrichment increases the relative amount of GLA and/or SDA in the oil (compared to all fatty acids present in the oil) as compared to the amount of GLA and/or SDA in the oil before enrichment.

In one embodiment, the oil comprising 18-carbon fatty acids is enriched by a method comprising selectively crystallizing at least a portion of fatty acids other than GLA and SDA and separating the crystallized fatty acids from the oil to form a first enriched oil. In some embodiments, the method comprises contacting the oil with a solvent system, said solvent system comprising acetone and optionally water. In some embodiments, the solvent system comprises acetone and water in a volume ratio of about 99.9:0.1 to about 90:10, for example about 99.9:0.1, about 99.8:0.2, about 99.7:0.3, about 99.6:0.4, about 99.5:0.5, about 99.4:0.6, about 99.3:0.7, about 99.2:0.8, about 99.1:0.9, about 99:1, about 98.5:1.5, about 98:2, about 97.5:2.5, about 97:3, about 96.5:3.5, about 96:4, about 95.5:4.5, about 95:5, about 94.5:5.5, about 94:6, about 93.5:6.5, about 93:7, about 92.5:7.5, about 92:8, about 91.5:8.5, about 91:9, about 90.5:9.5, or about 90:10. In some embodiments, the solvent system comprises acetone, water and a non-polar aprotic solvent such as heptane in a volume ratio of about 92:4:4 to about 99:0.5:0.5, for example about 92:4:4, about 94:3:3, about 96:2:2, about 98:1:1, about 98.5:1:0.5, or about 99:0.5:0.5.

In one embodiment, the oil is contacted with the solvent system in an oil:solvent system volume ratio of about 1:99 to about 50:50, for example about 1:99, about 2:98, about 3:97, about 4:96, about 5:95, about 6:94, about 7:93, about 8:92, about 9:91, about 10:90, about 15:85, about 20:80, about 25:75, about 30:70, about 35:65, about 40:60, about 45:55 or about 50:50.

After the oil is contacted with the first solvent system, the mixture is allowed to sit for a sufficient time to allow crystallization to occur. Optionally, the mixture is cooled to a temperature of −78° C. to about 10° C., for example about −78° C., about −65° C., about −60° C., about −55° C., about −50° C., about −45° C., about −40° C., about −35° C., about −30° C., about −25° C., about −20° C., about −15° C., about −10° C., about −5° C., about 0° C., about 4° C., about 5 or about 10° C. The crystals are separated from the enriched oil by any suitable method known to those skilled in the art (e.g., filtration, cold filtration, etc.).

In some embodiments, the method comprises treating the oil or the first enriched oil with a second solvent system to produce a second enriched oil. In some embodiments, the second solvent system comprises a non-polar aprotic solvent such as heptane. In some embodiments, the oil or the first enriched oil is contacted with the solvent system in an oil:solvent system volume ratio of about 1:99 to about 50:50, for example about 1:99, about 2:98, about 3:97, about 4:96, about 5:95, about 6:94, about 7:93, about 8:92, about 9:91, about 10:90, about 15:85, about 20:80, about 25:75, about 30:70, about 35:65, about 40:60, about 45:55 or about 50:50.

After the oil or the first enriched oil is contacted with the second solvent system, the mixture is allowed to sit for a sufficient time to allow crystallization to occur. Optionally, the mixture is cooled to a temperature of −78° C. to about 10° C., for example about −78° C., about −65° C., about −60° C., about −55° C., about −50° C., about 15° C., about −40° C., about −35° C., about −30° C., about −25° C., about −20° C., about −15° C., about −10° C., about −5° C., about 0° C., about 4° C., about 5 or about 10° C. The crystals are separated from the second enriched oil by any suitable method known to those skilled in the art (e.g., filtration, cold filtration, etc.).

In one embodiment, the oil is enriched in 18-carbon fatty acid compounds by a method comprising:

(i) contacting the oil with a first solvent system comprising acetone, water and heptane in a volume ratio of about 98.5:1:0.5, wherein the volume ratio of oil to solvent system is about 10:90;

(ii) cooling the resulting mixture to a temperature of about −60° C.;

(iii) cold-filtering the resulting cooled mixture to produce a first enriched oil, said first enriched oil having relatively more GLA and SDA than the oil;

(iv) contacting the first enriched oil with a second solvent system comprising a non-polar aprotic solvent such as heptane, wherein the volume ratio of first enriched oil:solvent system is about 10:90;

(v) cooling the resulting mixture to a temperature of about −60° C.; and (vi) cold-filtering the resulting cooled mixture to produce a second enriched oil, wherein GLA and SDA are present in the second enriched oil in amounts (relative to all fatty acids in the composition) greater than in the corresponding first enriched oil and the oil.

In some embodiments, the relative amount of GLA is increased by about 3% to about 500%, for example about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 150%, about 175%, about 200%, about 225%, about 250%, about 275%, about 300%, about 325%, about 350%, about 375%, about 400%, about 425%, about 450%, about 475%, or about 500%.

In some embodiments, the enriched oil comprises at least about 15% GLA compared to all fatty acids present in the enriched oil, for example at least about 15%, at least about 16%, at least about 17%, at least about 18%, at least about 19%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more than about 95% of all the fatty acids present in the enriched oil.

In some embodiments, the relative amount of SDA is increased by about 3% to about 500%, for example about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 150%, about 175%, about 200%, about 225%, about 250%, about 275%, about 300%, about 325%, about 350%, about 375%, about 400%, about 425%, about 450%, about 475%, or about 500%.

In some embodiments, the enriched oil comprises at least about 2% SDA compared to all fatty acids present in the enriched oil, for example at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, or more than 25% of all the fatty acids present in the enriched oil.

In some embodiments, the ratio of GLA to SDA (GLA: SDA) in the enriched oil is less than, about equal to, or greater than the ratio of GLA to SDA in the oil before enrichment is performed. In some embodiments, the enriched oil has a GLA:SDA ratio of about 1:1 to about 20:1, for example about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1.

Enrichment of 20-Carbon Fatty Acids

In some embodiments, the oil comprising 18-carbon fatty acids (e.g., plant seed oil) is subjected to the elongation process, and the resulting composition comprising 20-carbon fatty acids is then enriched such that the enriched composition contains comparatively more 20-carbon fatty acids than before the enrichment process is performed. Enrichment of the 20-carbon fatty acid composition may occur regardless of whether or not the oil comprising 18-carbon fatty acids and/or 18-carbon fatty acid triglycerides is enriched as previously described.

In one embodiment, the composition comprising 20-carbon fatty acids is enriched by separating at least a portion of fatty acids having more or less than 20 carbons (e.g., GLA and/or SDA) from the oil. In one embodiment, the enrichment increases the relative amount of DGLA and/or ETA in the oil compared to all fatty acids present in the composition as compared to the amount of DGLA and/or ETA in composition before enrichment.

In one embodiment, the composition comprising 20-carbon fatty acids is enriched according to a method comprising contacting the composition with a solvent system comprising a non-polar aprotic solvent such as heptane, cooling the resulting mixture to a temperature of about −78° C. to about 10° C. for a sufficient time to allow crystals to form, and separating the crystals from the enriched composition comprising 20-carbon fatty acids by any suitable method including, for example, cold-filtering.

In some embodiments, the enriched 20-carbon fatty acid composition is subjected to further purification. In one embodiment, the further purification comprises chromatographic separation (e.g., normal phase chromatography using silica gel and a solvent system beginning with 98:2:1 cyclohexane:ether:acetic acid and slowly increasing the amount of ether in the solvent system until the 20-carbon fatty acid(s) elute). In another embodiment, the further purification comprises contacting the enriched 20-carbon fatty acid composition with a second solvent system comprising a non-polar aprotic solvent such as heptane, cooling the resulting mixture to a temperature of about −78° C. to about 10° C., and separating the crystals from the enriched composition comprising 20-carbon fatty acids by any suitable method including, for example, cold-filtering.

In one embodiment, the enriched 20-carbon fatty acid composition has a ratio of 20-carbon omega-6 fatty acids to 20-carbon omega-3 fatty acids that is greater than the ratio of 18-carbon omega-6 fatty acids to 18-carbon omega-3 fatty acids in the starting oil. In one embodiment, the composition comprising 20-carbon fatty acids has a ratio of omega-6 fatty acids to omega-3 fatty acids of about 1:1 to about 10:1, for example about 1:1, about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, or about 10:1. In one embodiment, the ratio of omoega-6 fatty acids to omega-3 fatty acids in the composition is about 5:1.

Accordingly in one embodiment represented schematically by FIG. 1, an oil containing GLA and SDA (e.g., 18.1% by weight) is enriched by a winterization process by contacting the oil with about 9 mass equivalents of a solvent system consisting of acetone with 1% added water and 0.5% added heptane, and the mixture cooled to −60° C. The resulting enriched oil is further enriched in a winterization step by contacting the enriched oil with heptane, cooling to −60° C., and collecting the twice-enriched oil. In one embodiment shown in the right-hand pathway of FIG. 1, the twice-enriched oil is purified by preparatory HPLC to provide a purified composition comprising GLA and SDA. This material is then esterified to form methyl esters, reduced to form primary alcohols, mesylated to for primary mesylates, elongated by addition of diester malonate, hydrolyzed to form the corresponding di-acids, and decarboxylated to form a composition comprising DGLA and ETA (approx. 70% fatty acids).

In an alternate embodiment shown in the left-hand pathway of FIG. 1, the twice-enriched oil is esterified, reduced, mesylated, elongated, hydrolyzed, and decarboxylated to produce a composition comprising DGLA and ETA (70% fatty acids). This composition is then purified by preparatory HPLC to produce a purified composition comprising DGLA and SDA.

Pharmaceutical Compositions

In various embodiments, the invention provides pharmaceutical compositions, for example orally deliverable compositions, comprising DGLA, ETE, ETA, 15-OH-ETA, 15-HETrE or mixtures thereof. In one embodiment, the compositions comprise a therapeutically effective amount of DGLA, ETE, ETA, 15-OH-ETA, 15-HETrE, or a combination thereof. In one embodiment, the pharmaceutical composition comprises about 0.1% to about 99%, about 1% to about 95%, about 5% to about 90% by weight DGLA, ETE, ETA, 15-OH-ETA, 15-HETrE, or a combination thereof.

In one embodiment, the pharmaceutical composition comprises about at least about 70%, at least about 80% or at least about 90%, by weight, DGLA, ETE, ETA, 15-OH-ETA, 15-HETrE, or a combination thereof. In one embodiment, the pharmaceutical composition comprises at least about 50%, at least about 60%, at least about 70%, at least about 80% or at least about 90%, by weight, DGLA and ETA. In another embodiment, the pharmaceutical composition comprises at least about 50%, at least about 60%, at least about 70%, at least about 80% or at least about 90%, by weight, DGLA, ETE and ETA. In one embodiment, the pharmaceutical composition comprises at least about 50%, at least about 60%, at least about 70%, at least about 80% or at least about 90%, by weight, 15-OH-ETA and 15-HETrE.

In one embodiment, the pharmaceutical composition further comprises an additional active agent. In one embodiment, the pharmaceutical composition comprises an amount of the additional active agent that is less than the generally recognized therapeutically effective amount for that agent. In one embodiment, the pharmaceutical composition comprises an amount of the additional active agent that is equal to or greater than the generally recognized therapeutically effective amount for that agent.

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In some embodiments, compositions of the invention are in the form of orally deliverable dosage forms or units. Non-limiting examples of suitable dosage forms include tablets (e.g. suspension tablets, bite suspension tablets, rapid dispersion tablets, chewable tablets, etc), caplets, capsules (e.g. a soft or a hard gelatin capsule or HPMC capsule), lozenges, sachets, cachets, troches, pellets, suspension, elixirs, syrups or any other solid dosage form reasonably adapted for oral administration.

Alternatively, compositions of the invention can also be formulated for rectal, topical, or parenteral (e.g. subcutaneous, intramuscular, intravenous and intradermal or infusion) delivery.

In another embodiment, compositions of the invention comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition. By way of example only, a pharmaceutical composition according to the present disclosure may comprise one or more of: antioxidants, surfactants, preservatives, flavouring agents, co-solvents, viscosity aids, suspension aids, and lipophilic phases.

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, niacinamide, and the like. In one embodiment, the pharmaceutical composition comprises about 0.01 wt. % to about 2 wt. % of an antioxidant, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

The compositions and formulations disclosed herein may be used in the treatment of diseases and/or disorders including, without limitation, inflammatory diseases, cardiovascular diseases, respiratory diseases, neurological diseases, cancer, psychiatric diseases and skin diseases. In one embodiment, the method comprises administering a pharmaceutical composition as disclosed herein to a subject once per day, twice per day, three times per day, or more than three times per day.

As used herein, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Preparation of Composition Enriched in 18-Carbon Fatty Acids

Ten grams of black currant seed oil was saponified by heating the oil for three hours at 68° C. in a 3.75 M sodium hydroxide in ethanol/water (1:1) with 5 mM disodium ethylenediaminetetraacetic acid. After cooling, the solution was acidified to pH ~2 with 3 M hydrochloric acid. The organic components were extracted with heptane, dried over magnesium sulfate, and concentrated to provide free fatty acids in yields >90%. When analyzed by gas chromatography, the black currant seed oil was determined to consist of free fatty acids according to Table 1, below. The ratio of 18-carbon omega-6 fatty acids to 18-carbon omega-3 fatty acids in the starting oil was 63.60:14.78, or about 4.3:1.

TABLE 1

Composition of Black Currant Seed Oil.

| Component | Lipid Number | Retention Time (min, relative to palmitic acid) | Amount* |
|---|---|---|---|
| Palmitic acid | 16:1ω-7 | 1.00 | 6.93% |
| Stearic acid | 18:0 | 1.38 | 1.75% |
| Oleic acid | 18:1ω-9 | 1.46 | 10.89% |
| Unknown-1 | — | 1.47 | 0.84% |
| Linoleic acid | 18:2ω-6 | 1.63 | 49.51% |
| GLA | 18:3ω-6 | 1.75 | 14.09% |
| ALA | 18:3ω-3 | 1.83 | 12.63% |
| SDA | 18:4ω-3 | 1.98 | 2.15% |
| Unknown-2 | — | 2.10 | 1.2% |

*As determined by gas chromatography
**ND: not detected

The black currant seed oil fatty acid composition was then treated with a solvent system of 98.5:1:0.5 (v/v/v) acetone/water/heptane and cooled rapidly to −60° C. The volume ratio of oil to solvent system was 10:90. After 1-2 hours at −60° C., the slurry was rapidly cold-filtered. The enriched oil had a composition as shown in Table 2, below. The ratio of 18-carbon omega-6 fatty acids to 18-carbon omega-3 fatty acids decreased from about 4.2:1 to 70.51:22.58, or about 3.1:1

TABLE 2

Composition of Enriched Black Currant Seed Oil.

| Component | Lipid Number | Initial Amount* | Enriched Amount* |
|---|---|---|---|
| Palmitic acid | 16:1ω-7 | 6.93% | ND** |
| Stearic acid | 18:0 | 1.75% | ND** |
| Oleic acid | 18:1ω-9 | 10.89% | 4.74% |
| Unknown-1 | — | 0.84% | 1.11% |
| Linoleic acid | 18:2ω-6 | 49.51% | 38.65% |
| GLA | 18:3ω-6 | 14.09% | 31.86% |
| ALA | 18:3ω-3 | 12.63% | 18.47% |
| SDA | 18:4ω-3 | 2.15% | 4.11% |
| Unknown-2 | — | 1.2% | 0.66% |

*As determined by gas chromatography
**ND: not detected

A total of 4 g of enriched oil was recovered; 1.27 g of which was GLA (31.75% by weight). This represented an 85% recovery of GLA compared to the raw black currant seed oil.

The crystallized solids were rich in palmitic acid (10.8%), stearic acid (2.73%), oleic acid (14.96%), linoleic acid (55.34%), and Unknown-2 (1.46%) as compared to the raw black currant seed oil, while the crystallized solids were relatively poor in Unknown-1 (not detected), GLA (4.73%), ALA (9.14%) and SDA (0.84%). By comparison, enrichment in a solvent system consisting of only acetone and water (99:1 v/v) removed less palmitic acid, stearic acid, oleic acid, linoleic acid, and Unknown-2 than the ternary solvent system, as shown in column C of Table 3, below. The ternary solvent system was also surprisingly more effective at removing palmitic acid, oleic acid, Unknown-1, and Unknown-2 levels than a two-step process where the filtrate resulting from an acetone/water (99:1 v/v) enrichment process was subsequently treated to a second enrichment process using pure heptane (column D, Table 3).

TABLE 3

Comparison of Enrichment With and Without Heptane Co-Solvent.

| Component | Lipid Number | (A) Initial Amount* | (B) Enriched Amount* Acetone/ Water/ Heptane (98.5:1:0.5) | (C) Enriched Amount* Acetone/ Water (99:1) | (D) Enriched Amount* Acetone/ Water (99:1), then Heptane |
|---|---|---|---|---|---|
| Palmitic acid | 16:1ω-7 | 6.93% | ND** | 0.63% | 0.73% |
| Stearic acid | 18:0 | 1.75% | ND** | 0.1% | ND** |
| Oleic acid | 18:1ω-9 | 10.89% | 4.74% | 12.13% | 6.85% |
| Unknown-1 | — | 0.84% | 1.11% | 0.25% | 1.35% |
| Linoleic acid | 18:2ω-6 | 49.51% | 38.65% | 52.71% | 23.08% |
| GLA | 18:3ω-6 | 14.09% | 31.86% | 16.85% | 51.09% |
| ALA | 18:3ω-3 | 12.63% | 18.47% | 13.77% | 8.2% |
| SDA | 18:4ω-3 | 2.15% | 4.11% | 2.25% | 6.76% |
| Unknown-2 | — | 1.2% | 0.66% | 1.31% | 1.73% |

*As determined by gas chromatography
**ND: not detected

Two grams of the composition enriched by crystallization with the acetone/water/heptane (98.5:1:0.5 v/v/v) solvent system was then subjected to a second enrichment process by mixing with heptane. The mixture was rapidly cooled to −60° C. and held for 1-2 hours. The solids were filtered, and the resulting enriched oil had the composition shown in Table 4, below. The ratio of 18-carbon omega-6 fatty acids to 18-carbon omega-3 fatty acids was 73.4:19.51, or about 3.75:1. This ratio is less than the ratio of omega-6 to omega-3 18-carbon fatty acids in the original black currant seed oil (about 4.3:1), but greater than the ratio after the first enrichment step (about 3.1:1).

TABLE 4

Composition of Final Enriched Oil.

| Component | Lipid Number | Initial Amount* | Enriched Amount* |
|---|---|---|---|
| Palmitic acid | 16:1ω-7 | 6.93% | ND** |
| Stearic acid | 18:0 | 1.75% | ND** |
| Oleic acid | 18:1ω-9 | 10.89% | 5.95% |
| Unknown-1 | — | 0.84% | ND** |
| Linoleic acid | 18:2ω-6 | 49.51% | 25.3% |
| GLA | 18:3ω-6 | 14.09% | 48.1% |
| ALA | 18:3ω-3 | 12.63% | 13.18% |
| SDA | 18:4ω-3 | 2.15% | 6.33% |
| Unknown-2 | — | 1.2% | 0.88% |

*As determined by gas chromatography
**ND: not detected

A total of 1.02 g of enriched oil was recovered. This represented a 77% recovery of GLA compared to the first enriched oil, and 65% recovery of GLA compared to the starting oil. The GLA:SDA ratio in the enriched composition increased to about 7.6:1 compared to the GLA:SDA ratio in the raw blackcurrant seed oil (about 6.6:1). The ratio of GLA:SDA+ALA increased from about 0.95:1 in the raw blackcurrant seed oil to about 2.5:1 in the enriched oil.

The crystallized solids consisted of oleic acid (5.63%), linoleic acid (58.25%), GLA (8.59%), ALA (26.09%), SDA (1.12%) and Unknown-2 (0.31%).

Example 2

Preparation of Composition Enriched in 20-Carbon Fatty Acids

The composition prepared according to Example 1 was diluted 5-fold with heptane. The resulting solution was treated with a large excess (~10 equivalents) of methyl hypochlorite in methanol (freshly prepared) at 100° C. for 2 hours. The resulting 18-carbon fatty acid methyl esters were produced in 92% yield and were 97% pure by GC analysis.

The mixture of 18-carbon fatty acid methyl esters was added dropwise to a 0° C. mixture of 2 equivalents of lithium aluminum hydride in anhydrous MTBE that had been allowed to stir at room temperature for 3 hours prior. After addition of the methyl ester mixture was complete, the slurry was allowed to warm to room temperature, after which it was allowed to stir overnight. After quenching with wet sodium sulfite (1 mL water/g of sodium sulfite) over ice and subsequent work-up, the resulting 18-carbon fatty acid primary alcohols were recovered at 84% yield and 97% purity as determined by GC.

The mixture of 18-carbon fatty acid primary alcohols was diluted in dichloromethane and cooled to 0° C. 1.5 equivalents of triethylamine were added dropwise, followed by 1.1 equivalents of methanesulfonyl chloride. The mixture was stirred overnight at 0° C. Thereafter, water was added and the resulting mesylated 18-carbon fatty acid primary alcohols were recovered in 93% yield and 91% purity as determined by GC.

Dimethyl malonate was deprotonated by dropwise addition to 1 equivalent of sodium hydride in THF at 0° C. After heating to 60° C. for 3 hours and re-cooling to 0° C., 1 equivalent of the mixture of mesylated 18-carbon fatty acid primary alcohols was added. After refluxing at 80° C. for 40 hours, the reaction was quenched with water and acidified to pH ~2 with HCl. The THF was evaporated before the organic fraction was extracted in dichloromethane, dried over magnesium sulfate, and concentrated to yield 88% of a mixture of 20-carbon fatty acid di-esters having a purity of 86% as determined by NMR.

The mixture of 20-carbon fatty acid di-esters was hydrolyzed by combining with a 1:1 ethanol:NaOH (2 M) solution and heating to 40° C. After the reaction was complete as determined by TLC, the reaction mixture was acidified to pH ~3-4 with citric acid before extraction with ether. Performing an organic (ether) wash before acidification was found to remove the desired products. Workup by acidification then ether extraction resulted in recovery of the mixture of 20-carbon free fatty di-acids in 80% yield at 84% purity as determined by GC.

The 20-carbon free fatty di-acids were converted into the desired 20-carbon free fatty acids by dissolving the mixture of di-acids in toluene and refluxing at 140° C. overnight. After cooling to room temperature, the mixture was filtered through a Celite plug and concentrated without further workup to yield a composition comprising 20-carbon free fatty acids in 75% yield at 70% purity as determined by GC. The distribution of free fatty acids in the composition is shown in Table 5, below.

TABLE 5

Fatty Acids in Elongated Oil.

| 18-Carbon Component | Lipid Number | Initial Amount* | 20-Carbon Component | Lipid Number | Final Amount* |
|---|---|---|---|---|---|
| Palmitic acid | 16:1ω-7 | ND** | Vaccenic acid | 18:1ω-7 | ND** |
| Stearic acid | 18:0 | ND** | Arachidic acid | 20:0 | ND** |
| Oleic acid | 18:1ω-9 | 5.3% | Eicosenoic acid | 20:1ω-9 | 5.02% |
| Unknown-1 | — | 1.11% | Elongated Unknown-1 | — | 1.34% |

TABLE 5-continued

Fatty Acids in Elongated Oil.

| 18-Carbon Component | Lipid Number | Initial Amount* | 20-Carbon Component | Lipid Number | Final Amount* |
|---|---|---|---|---|---|
| Linoleic acid | 18:2ω-6 | 32.31% | Eicosadienoic acid | 20:2ω-6 | 30.89% |
| GLA | 18:3ω-6 | 43.47% | DGLA | 20:3ω-6 | 43.08% |
| ALA | 18:3ω-3 | 11.78% | ETE | 20:3ω-3 | 12.96% |
| SDA | 18:4ω-3 | 5.25% | ETA | 20:4ω-3 | 5.69% |
| Unknown-2 | — | 0.8% | Elongated Unknown-2 | — | 1.02% |

*As determined by gas chromatography
**ND: not detected

About 20% of the final composition consisted of 18-carbon fatty acid primary alcohols, indicating that formation of the mesylate derivatives was incomplete or the mesylates were unstable and degraded before elongation by deprotonated dimethyl malonate.

Example 3

Purification of 20-Carbon Fatty Acid Compositions

Three grams of an elongated fatty acid composition prepared according to the process of Example 2 was purified by addition of heptane, cooling to −60° C., holding the mixture at −60° C. for 1-2 hours, and then cold-filtering the crystals. The resulting filtrate (2.18 g) was enriched in DGLA and ETA, while all other free fatty acid components were reduced, as shown in Table 6, below.

TABLE 5

Fatty Acids in Elongated Oil.

| Elongated Component | Lipid Number | Initial Amount* | Enriched Amount* | Source Fatty Acid |
|---|---|---|---|---|
| Vaccenic acid | 18:1ω-7 | ND** | ND** | palmitic acid |
| Arachidic acid | 20:0 | ND** | ND** | stearic acid |
| Eicosenoic acid | 20:1ω-9 | 5.17% | 4.53% | oleic acid |
| Elongated Unknown-1 | — | 1.22% | 1.37% | unknown-1 |
| Eicosadienoic acid | 20:2ω-6 | 31.6% | 24.69% | linoleic acid |
| DGLA | 20:3ω-6 | 43.16% | 52.16% | GLA |
| ETE | 20:3ω-3 | 12.45% | 9.02% | ALA |
| ETA | 20:4ω-3 | 5.4% | 7.32% | SDA |
| Elongated Unknown-2 | — | 1.% | 0.9% | unknown-2 |

*As determined by gas chromatography
**ND: not detected

The filtered solids (0.82 g) included, among other components, 23% DGLA and 3% ETA.

Further purification of the enriched oil prepared above was accomplished by silica gel chromatography. No solvent system was found suitable to separate the free fatty acids into separate eluents. However, some of the impurities were removed using an increasingly non-polar solvent gradient. Two grams of the enriched composition described above in this Example 3 were loaded onto a silica gel plug. Starting with a ternary solvent system consisting of 98:2:1 cyclohexane:ether:acetic acid, the relative amount of ether was slowly increased until free fatty acids eluted. Although excess 18-carbon free fatty acid primary alcohols co-eluted, some purified fractions were collected and concentrated to yield 0.1 g of 90% pure (by GC) 20-carbon free fatty acids. Of the fatty acids present in this material, 52.22% was DGLA, and 5.05% was ETA, as shown in Table 6, below.

Another set of fractions containing 20-carbon free fatty acids and residual 18-carbon fatty acid primary alcohols was collected and concentrated to yield 980 mg of compounds, 80% of which (by GC) were 20-carbon free fatty acid compounds. Of the fatty acids present in this fraction 53.9% was DGLA and 7.3% was ETA, as shown in Table 6, below.

The remaining compounds were flushed from the silica gel plug with pure ether, combined and concentrated to yield 980 mg of material, 35% of which was 20-carbon free fatty acids. Of the fatty acids present in this material, 46.56% was DGLA, and 5.17% was ETA, as shown in Table 6, below.

TABLE 6

Composition of Chromatography Fractions.

| Elongated Component | Lipid Number | Initial Amount* | First Fraction* | Second Fraction* | Flushed Fraction* |
|---|---|---|---|---|---|
| Vaccenic acid | 18:1ω-7 | ND** | ND** | ND** | ND** |
| Arachidic acid | 20:0 | ND** | ND** | ND** | ND** |
| Eicosenoic acid | 20:1ω-9 | 4.53% | 5.65% | 4.39% | 5.87% |
| Elongated Unknown-1 | — | 1.37% | 1.42% | 1.1% | 1.24% |
| Eicosadienoic acid | 20:2ω-6 | 24.69% | 26.37% | 23.52% | 30.54% |
| DGLA | 20:3ω-6 | 52.16% | 52.22% | 53.86% | 46.56% |
| ETE | 20:3ω-3 | 9.02% | 8.32% | 8.88% | 9.72% |
| ETA | 20:4ω-3 | 7.32% | 5.05% | 7.31% | 5.17% |
| Elongated Unknown-2 | — | 0.9% | 0.96% | 0.94% | 0.9% |

*As determined by gas chromatography
**ND: not detected

Further purification of the second fraction shown in Table 6 above was performed by mixing with heptane, cooling to −60° C., holding the mixture at −60° C. for 1-2 hours, and then cold-filtering the solids (330 mg) away from the supernatant fluid (600 mg). As shown in Table 7 below, the filtrate was enriched in DGLA and ETA, while the relative amounts of eicosenoic acid, elongated unknown-1, eicosadienoic acid, ETE, and elongated unknown-2 were all reduced.

TABLE 7

Purification of Second Fraction by Heptane.

| Elongated Component | Lipid Number | Initial Amount* | Enriched Amount* |
|---|---|---|---|
| Vaccenic acid | 18:1ω-7 | ND** | ND** |
| Arachidic acid | 20:0 | ND** | ND** |
| Eicosenoic acid | 20:1ω-9 | 4.39% | 3.79% |
| Elongated Unknown-1 | — | 1.1% | 0.99% |
| Eicosadienoic acid | 20:2ω-6 | 23.52% | 18.96% |
| DGLA | 20:3ω-6 | 53.86% | 59.99% |
| ETE | 20:3ω-3 | 8.88% | 7.21% |
| ETA | 20:4ω-3 | 7.31% | 8.44% |
| Elongated Unknown-2 | — | 0.94% | 0.61% |

*As determined by gas chromatography
**ND: not detected

The filtered solids included some free fatty acid compounds, 38% of which were DGLA and 4.8% of which were ETA as determined by gas chromatography.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

Also provided by the present invention are embodiments set forth in paragraphs [0102-[0127]:

A process for producing 20-carbon fatty acids from a plant seed oil, the process comprising:
  a.) providing a plant seed oil comprising fatty acids, wherein the fatty acids include 18-carbon fatty acids;
  b.) elongating at least a portion of the 18-carbon fatty acids by two carbon atoms to produce 20-carbon fatty acids, optionally by contacting the fatty acids with an enzyme optionally selected from the group consisting of elongase; and
  c.) optionally esterifying at least a portion of the 20-carbon fatty acids.

The process of paragraph [0102], wherein the 18-carbon fatty acids in the plant seed oil include a plurality of 18-carbon fatty acids.

The process of paragraph [0102], wherein the 18-carbon fatty acids include one or more of SDA, GLA, and ALA, and the 20-carbon fatty acids include one or more of ETA, ETE and DGLA.

The process of paragraph [0102] further comprising prior to step b.) extracting the 18-carbon fatty acids from the plant seed oil, optionally with an organic solvent extraction or a $CO_2$ supercritical fluid extraction ($CO_2$-SFE).

The process of paragraph [0102] further comprising purifying the 20-carbon fatty acids, optionally by urea fractionization, low-temperature crystallization, chromatographic separation, HPLC, or distillation.

The process of paragraph [0102], wherein the 20-carbon fatty acids are purified to produce 20-carbon fatty acids having a purity of at least 30%, at least 40%, at least 50%, at least 60%, at least 70%, at least 80%, at least 90%, or greater than 90%.

The process of paragraph [0102], wherein the plant seed oil is selected from the group comprising: Echium seed oil, blackcurrant seed oil, borage seed oil, evening primrose seed oil, hackelia seed oil, trichodesma seed oil, buglossoides seed oil, and combinations thereof.

The process of paragraph [0102] further comprising deodorizing the 20-carbon fatty acids, optionally by mixing the 20-carbon fatty acids with a mixture of silica and charcoal or by passing the 20-carbon fatty acids through a celite filter.

The process of paragraph [0105] further comprising esterifying the DGLA, ETE and/or ETA, optionally by contacting the DGLA with an alcohol and an acid to produce the DGLA esters, to produce DGLA, ETE and/or ETA esters, the esters optionally selected from the group consisting of alkyl esters, heteroalkyl esters, aryl esters, heteroaryl esters, methyl esters, ethyl esters, propyl esters, isopropyl esters, butyl esters, isobutyl esters, t-butyl esters, and combinations thereof.

The process of paragraph [0102], wherein the ratio of produced 20-carbon fatty acids to starting 18-carbon fatty acids is about 1:1.

The process of paragraph [0102], wherein the 20-carbon fatty acids produced in step b.) has a molar ratio of 20-carbon omega-6 fatty acids to 20-carbon omega-3 fatty acids that is greater than an 18-carbon fatty acid molar ratio associated with the plant seed oil of step a.), said 18-carbon fatty acid molar ratio defined by a molar ratio of 18-carbon omega-6 fatty acids to 18-carbon omega-3 fatty acids, and the 18-carbon fatty acid molar ratio.

12. The process of paragraph [0103], wherein two or more 18-carbon fatty acids in the plant seed oil are elongated simultaneously.

A composition comprising the fatty acids produced by the process of paragraph [0102].

The composition of paragraph [0114], wherein the composition comprises at least 30%, at least 40%, at least 50%, at least 60%, at least 70%, at least 80%, at least 90%, or greater than 90% of one or more of DGLA, ETA, and ETE.

A method for elongating fatty acids in a plant seed oil, the method comprising:
  a.) providing a plant seed oil comprising fatty acids, wherein the fatty acids include 18-carbon fatty acids;
  b.) optionally extracting the 18-carbon fatty acids; and
  c.) elongating the fatty acids by two carbon atoms.

The method of paragraph [0116], wherein two or more 18-carbon fatty acids in the plant seed oil are elongated simultaneously.

A process for producing a composition comprising DGLA, ETE and ETA, the process comprising:
  a.) providing a plant seed oil comprising fatty acids, wherein the fatty acids include SDA, ALA and GLA;
  b.) enriching SDA, ALA and GLA in the plant seed oil;
  c.) elongating the SDA, ALA and GLA simultaneously by two carbon atoms, wherein a composition comprising DGLA, ETE and ETA is produced from SDA, ETE and GLA; and
  d.) optionally enriching the composition comprising DGLA, ETE and ETA.

A composition produced by the process of paragraph [0118], wherein the composition comprises at least 50 wt. % of DGLA, ETE, ETA, or a combination thereof.

A composition produced by the process of paragraph [0118], wherein the composition comprises a ratio of DGLA to ETE and ETA of about 1:10 to about 10:1.

The method of paragraph [0118], wherein step b.) comprises (i) contacting the plant seed oil with a solvent system consisting of acetone, water and heptane (ii) cooling the resulting mixture to a temperature sufficient to induce crystal formation, and (iii) separating the crystals from the plant seed oil-solvent system mixture to produce a plant seed oil enriched in SDA, ALA and GLA.

The method of paragraph [0118], wherein step c.) comprises:
  (i) esterifying the SDA, ALA and GLA to form SDA, ALA and GLA esters;
  (ii) reducing the SDA, ALA and GLA esters to form SDA, ALA and GLA primary alcohols;
  (iii) mesylating the SDA, ALA and GLA primary alcohols to form SDA, ALA and GLA mesylates;
  (iv) contacting the SDA, ALA and GLA mesylates with a $C_2$-elongation block, wherein said $C_2$-elongation block is a deprotonated malonic diester to form elongated SDA, ALA and GLA diesters;
  (v) hydrolyzing the elongated SDA, ALA and GLA diesters to form elongated SDA, ALA and GLA diacids; and
  (vi) decarboxylating the elongated SDA, ALA and GLA diacids to form DGLA, ETE and ETA.

The method of paragraph [0118], wherein step d.) comprises: (i) contacting the composition comprising DGLA, ETE and ETA with a solvent system comprising heptane (ii) cooling the resulting mixture to a temperature sufficient to induce crystal formation, and (iii) separating the crystals from the composition-solvent system mixture to produce an enriched composition comprising DGLA, ETE and ETA.

A process for producing 20-carbon fatty acids from a plant seed oil, the process comprising:
(a) providing a plant seed oil containing 18-carbon fatty acid triglycerides,
(b) digesting glycerol backbones of the 18-carbon fatty acid triglycerides by exposing the plant seed oil to lipase to form an oil comprising 18-carbon free fatty acids,
(c) optionally concentrating one or more of the 18-carbon free fatty acids from the oil,
(d) treating the oil or the optionally concentrated 18-carbon free fatty acids with elongase to produce 20-carbon fatty acids,
(e) esterifying at least a portion of the 20-carbon fatty acids, and
(f) optionally concentrating at least a portion of the esterified 20-carbon fatty acids.

A pharmaceutical composition comprising DGLA, ETE and ETA, wherein a ratio of DGLA to ETE and ETA is about 1:10 to about 10:1.

The pharmaceutical composition of paragraph [0125], wherein DGLA, ETE and ETA, combined, comprise at least 70%, 80% or 90%, by weight, of all fatty acid components of the composition.

A method of treating an inflammatory, cardiovascular, respiratory, neurological, cancer, psychiatric or skin disease in a subject in need thereof, comprising administering to the subject the pharmaceutical composition of paragraph [0125].

What is claimed is:

1. A process for producing 20-carbon fatty acids from a plant seed oil comprising 18-carbon fatty acids, the process comprising;
    providing a plant seed oil comprising fatty acids, wherein the fatty acids include 18-carbon fatty acids; and
    elongating at least a portion of the 18-carbon fatty acids present in the plant seed oil by two carbon atoms to produce 20-carbon fatty acids.

2. The process of claim 1 wherein said elongating step comprises contacting the plant seed oil comprising the 18-carbon fatty acids with an enzyme.

3. The process of claim 2 wherein the enzyme comprises elongase.

4. The process of claim 3 further comprising a step of esterifying at least a portion of the 20-carbon fatty acids.

5. The process of claim 1, wherein the plant seed oil comprises a plurality of different 18-carbon fatty acids.

6. The process of claim 5, wherein the plurality of different 18-carbon fatty acids comprises one or more of SDA, GLA, and ALA, and the 20-carbon fatty acids comprise one or more of ETA, ETE and DGLA.

7. The process of claim 1, wherein the plant seed oil is selected from the group comprising: Echium seed oil, blackcurrant seed oil, borage seed oil, evening primrose seed oil, hackelia seed oil, trichodesma seed oil, buglossoides seed oil, and combinations thereof.

8. The process of claim 7 further comprising deodorizing the 20-carbon fatty acids, optionally by mixing the 20-carbon fatty acids with a mixture of silica and charcoal or by passing the 20-carbon fatty acids through a celite filter.

9. The process of claim 6 further comprising esterifying the DGLA, ETE and/or ETA, optionally by contacting the DGLA with an alcohol and an acid to produce DGLA, ETE and/or ETA esters, the esters optionally selected from the group consisting of alkyl esters, heteroalkyl esters, aryl esters, heteroaryl esters, methyl esters, ethyl esters, propyl esters, isopropyl esters, butyl esters, isobutyl esters, t-butyl esters, and combinations thereof.

10. The process of claim 1, wherein the molar ratio of 20-carbon fatty acids produced to 18-carbon fatty acids in the plant seed oil is about 1:1.

11. The process of claim 1, wherein the 20-carbon fatty acids produced have a molar ratio of 20-carbon omega-6 fatty acids to 20-carbon omega-3 fatty acids that is greater than an 18-carbon fatty acid molar ratio in the plant seed oil, said 18-carbon fatty acid molar ratio defined by a molar ratio of 18-carbon omega-6 fatty acids to 18-carbon omega-3 fatty acids.

12. A composition comprising 20-carbon fatty acids produced by the process of of claim 1.

13. The composition of claim 12, comprising at least 50%, by weight, of one or more of DGLA, ETA, and ETE.

14. The process of claim 2, wherein two or more 18-carbon fatty acids in the plant seed oil are elongated simultaneously.

15. A process for producing a composition comprising DGLA, ETE and ETA, the process comprising:
    enriching SDA, ALA and GLA in a plant seed oil comprising SDA, ALA and GLA;
    simultaneously elongating the SDA, ALA and GLA each by two carbon atoms in the plant seed oil to provide DGLA, ETE and ETA; and
    optionally enriching the composition comprising DGLA, ETE and ETA.

16. A composition produced by the process of claim 15, wherein the composition comprises at least 50 wt. % of DGLA, ETE and/or ETA.

17. A composition produced by the process of claim 15, wherein the composition comprises a molar ratio of DGLA:ETE plus ETA of about 1:10 to about 10:1.

18. The process of claim 15 wherein the step of enriching SDA, ALA and GLA in the plant seed oil comprises (i) contacting the plant seed oil with a solvent system consisting of acetone, water and heptane (ii) cooling the resulting mixture to a temperature sufficient to induce crystal formation, and (iii) separating the crystals from the plant seed oil-solvent system mixture to produce a plant seed oil enriched in SDA, ALA and GLA.

19. The process of claim 15 wherein the step of simultaneously elongating the SDA, ALA and GLA each by two carbon atoms comprises:
    (i) esterifying the SDA, ALA and GLA to form SDA, ALA and GLA esters;
    (ii) reducing the SDA, ALA and GLA esters to form SDA, ALA and GLA primary alcohols;
    (iii) mesylating the SDA, ALA and GLA primary alcohols to form SDA, ALA and GLA mesylates;
    (iv) contacting the SDA, ALA and GLA mesylates with a $C_2$-elongation block, wherein said $C_2$-elongation block is a deprotonated malonic diester to form elongated SDA, ALA and GLA diesters;
    (v) hydrolyzing the elongated SDA, ALA and GLA diesters to form elongated SDA, ALA and GLA diacids; and
    (vi) decarboxylating the elongated SDA, ALA and GLA diacids to form DGLA, ETE and ETA.

20. The process of claim 15 wherein the optional step of enriching DGLA, ETE and ETA comprises (i) contacting the composition comprising DGLA, ETE and ETA with a solvent system comprising heptane (ii) cooling the resulting mixture to a temperature sufficient to induce crystal formation, and (iii) separating the crystals from the composition-solvent system mixture to produce an enriched composition comprising DGLA, ETE and ETA.

21. A process for producing 20-carbon fatty acids from a plant seed oil, the process comprising:
  (a) digesting glycerol backbones of 18-carbon fatty acid triglycerides in a plant seed oil by exposing the plant seed oil to lipase to form an oil comprising 18-carbon free fatty acids,
  (b) optionally concentrating one or more of the 18-carbon free fatty acids from the oil,
  (c) elongating the 18-carbon free fatty acids in the plant seed oil by contacting the plant seed oil with elongase to produce a plant seed oil comprising 20-carbon fatty acids,
  (d) esterifying at least a portion of the 20-carbon fatty acids, and
  (e) optionally concentrating at least a portion of the esterified 20-carbon fatty acids.

22. A pharmaceutical composition comprising DGLA, ETE and ETA having a molar ratio of DGLA to ETE plus ETA of about 1:10 to about 10:1.

23. The pharmaceutical composition of claim 22, wherein DGLA, ETE and ETA collectively comprise at least 70%, by weight, of all fatty acids present in the composition.

24. A method of treating an inflammatory, cardiovascular, respiratory, neurological, cancer, psychiatric or skin disease in a subject in need thereof, comprising administering to the subject a pharmaceutical composition of claim 22.

* * * * *